US008614793B2

(12) United States Patent
Tokhtuev et al.

(10) Patent No.: US 8,614,793 B2
(45) Date of Patent: Dec. 24, 2013

(54) FLOW CHAMBER FOR ONLINE FLUOROMETER

(75) Inventors: Eugene Tokhtuev, Duluth, MN (US); William M. Christensen, Hibbing, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/437,573

(22) Filed: Apr. 2, 2012

(65) Prior Publication Data
US 2013/0256557 A1 Oct. 3, 2013

(51) Int. Cl.
*G01N 21/00* (2006.01)

(52) U.S. Cl.
USPC .......................................... 356/436; 356/432

(58) Field of Classification Search
USPC .................. 356/432–442, 317, 246; 250/365, 250/336.1, 363.01, 200, 216, 573, 206, 373, 250/574, 576, 301, 302, 458.1, 459.1, 250/461.1, 461.2, 564, 372; 359/361, 350; 29/592.1, 592
See application file for complete search history.

(56) References Cited

U.S. PATENT DOCUMENTS

| | | | |
|---|---|---|---|
| 3,917,404 A | 11/1975 | Heiss | |
| 4,008,397 A | 2/1977 | Zdrodowski | |
| 4,440,497 A * | 4/1984 | Carey et al. | 356/246 |
| 4,750,837 A | 6/1988 | Gifford et al. | |
| 7,099,012 B1 | 8/2006 | Crawford et al. | |
| 7,550,746 B2 | 6/2009 | Tokhtuev et al. | |
| 7,652,267 B2 | 1/2010 | Tokhtuev et al. | |
| 7,989,780 B2 | 8/2011 | Tokhtuev et al. | |
| 2010/0084572 A1 | 4/2010 | Tokhtuev et al. | |
| 2010/0140503 A1 | 6/2010 | Sugiura et al. | |
| 2011/0195445 A1 | 8/2011 | Halden | |
| 2011/0240886 A1 | 10/2011 | Tokhtuev et al. | |
| 2011/0240887 A1 | 10/2011 | Christensen et al. | |
| 2011/0242539 A1 | 10/2011 | Christensen et al. | |

FOREIGN PATENT DOCUMENTS

WO 2012017380 A2 2/2012

OTHER PUBLICATIONS

Notification of Transmittal of the International Search Report and the Written Opinion of the International Searching Authority, or the Declaration of corresponding application PCT/US2013/034591, mailed Aug. 19, 2013, 11 pages.

* cited by examiner

*Primary Examiner* — Tri T Ton
(74) *Attorney, Agent, or Firm* — Fredrikson & Bryon, P.A.

(57) ABSTRACT

A fluorescence analysis system may include a sensor head that has a light source configured to emit light into a flow of fluid, a detector configured to detect fluorescent emissions from the flow of fluid, and a temperature sensor. The system may also include a flow chamber that includes a housing defining a cavity into which the sensor head can be inserted. In some examples, the housing is configured such that, when a flow of fluid enters the housing, the flow of fluid divides into at least a major stream passing adjacent the light source and the detector and a minor stream passing adjacent the temperature sensor. Such a flow chamber may direct fluid past different sensors components while inhibiting a build-up of solids particles, the generation of air locks, or other flow issues attendant with continuous or semi-continuous online operation.

20 Claims, 9 Drawing Sheets

FLOW CHAMBER FOR ONLINE FLUOROMETER

TECHNICAL FIELD

This disclosure relates to an optical sensor and, more particularly, to a flow chamber for an optical sensor that can be used for online optical measurements.

BACKGROUND

Aqueous chemical solutions are used in a variety of situations. For example, in different applications, aqueous cleaning solutions are used to clean, sanitize, and/or disinfect kitchens, bathrooms, schools, hospitals, factories, and other similar facilities. Aqueous cleaning solutions typically include one or more chemical species dissolved in water. The chemical species impart various functional properties to the water such as cleaning properties, antimicrobial activity, and the like.

Ensuring that an aqueous chemical solution is appropriately formulated for an intended application can help ensure that the solution provides suitable functional properties. For example, the functional properties of some aqueous cleaning solutions vary according to the temperature and the concentration of the chemical species dissolved in water, among other factors. Accordingly, measuring the different characteristics of the aqueous solution before use can be beneficial to understand the properties of the solution and to determine if adjustment is required. While samples of an aqueous solution can be extracted from a source and transported to a laboratory for analysis, such a technique does not always allow for rapid analysis of a solution, which would be helpful for time sensitive applications.

An optical sensor is one type of device that can be used to analyze an aqueous solution. When the optical sensor is implemented online to receive a sample directly from a source, the optical sensor may analyze the characteristics of the sample comparatively rapidly, providing timely feedback for monitoring and adjusting the properties of the solution. Ensuring that the optical sensor is appropriately configured to receive and process the sample on a continuous or semi-continuous basis may be useful for accurately and rapidly monitoring and/or adjusting the properties of the sample source.

SUMMARY

In general, this disclosure is directed towards optical sensors and optical-based techniques for determining a characteristic of a fluid such as, e.g., an aqueous chemical solution. In some examples, the optical sensor includes a flow chamber and a sensor head that is configured to be inserted into the flow chamber. The sensor head may be a fluorometer that is configured to emit light into a flow of fluid passing through the flow chamber and to detect fluorescent emissions from fluid. Depending on the application, the flow chamber may be configured such that, when the flow of fluid enters the flow chamber, the flow of fluid divides into at least a major stream passing adjacent a light source and a detector of the sensor head and a minor stream passing adjacent a temperature sensor of the sensor head. By dividing the fluid flow into a major stream and a minor stream, the flow chamber may direct the fluid past different sensors associated with the sensor head while inhibiting a build-up of solids particles, the generation of air bubbles or air locks, or other flow issues attendant with continuous or semi-continuous online operation.

In one example, a fluorescence analysis system is described that includes a sensor head and a flow chamber. The sensor head includes at least one light source configured to emit light into a flow of fluid, at least one detector configured to detect fluorescent emissions from the flow of fluid, and a temperature sensor configured to sense a temperature of the flow of fluid. The flow chamber includes a housing defining a cavity into which the sensor head is inserted, an inlet port extending through the housing and configured to communicate the flow of fluid from outside of the cavity to an interior of the cavity, and an outlet port extending through the housing and configured to communicate the flow of fluid from the interior of the cavity to back outside of the cavity. According to the example, the housing is configured such that, when the flow of fluid enters the housing via the inlet port, the flow of fluid divides into at least a major stream passing adjacent the light source and the detector and a minor stream passing adjacent the temperature sensor.

In another example, a flow chamber is described that includes a housing, an inlet port, and an outlet port. The housing defines a cavity configured to receive a sensor head and to position the sensor head in a flow of fluid for analysis, where the sensor head includes at least one light source configured to emit light into the flow of fluid, at least one detector configured to detect fluorescence emissions from the flow of fluid, and a temperature sensor configured to sense a temperature of the flow of fluid. The inlet port extends through the housing and configured to communicate the flow of fluid from outside of the cavity to an interior of the cavity. The outlet port extends through the housing and configured to communicate the flow of fluid from the interior of the cavity to back outside of the cavity. According to the example, the housing is configured such that, when the sensor head is inserted into the housing and the flow of fluid enters the housing via the inlet port, the flow of fluid divides into at least a major stream passing adjacent the light source and the detector and a minor stream passing adjacent the temperature sensor.

In another example, a fluorescence analysis system is described that includes means for detecting fluorescent emissions from a flow of fluid, means for sensing a temperature of the flow of fluid, and means for receiving and housing the means for detecting fluorescent emissions and the means for sensing the temperature. According to the example, the means for receiving and housing defines a plurality of fluid channels that include at least a major fluid channel configured to direct fluid adjacent the means for detecting fluorescent emissions and a minor fluid channel configured to direct fluid adjacent the means for sensing the temperature.

The details of one or more examples are set forth in the accompanying drawings and the description below. Other features, objects, and advantages will be apparent from the description and drawings, and from the claims.

DETAILED DESCRIPTION

Figure 1:
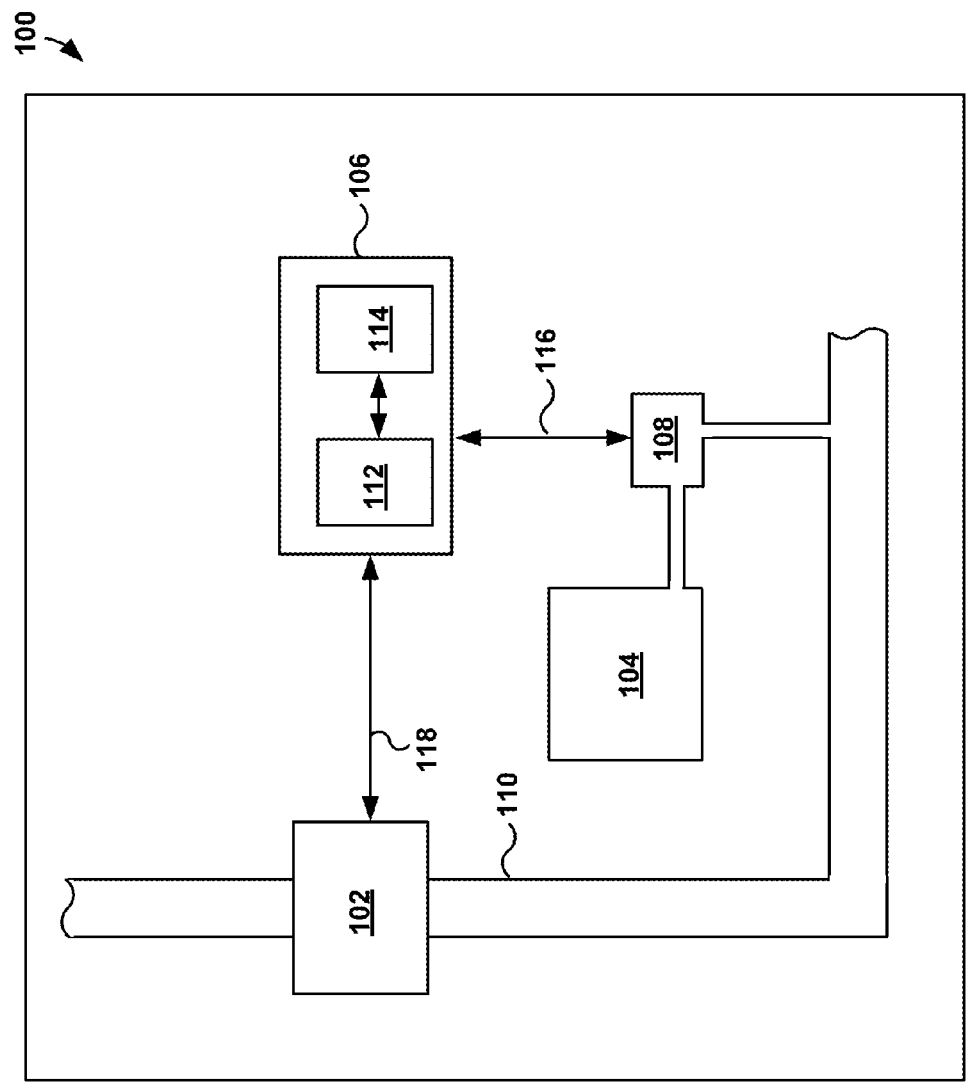
FIG. 1 is a diagram illustrating an example fluid system that includes an optical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Fluids with active chemical agents are used in a variety of different industries for a variety of different applications. For example, in the cleaning industry, fluid solutions that include chlorine or other active chemical agents are often used to clean and disinfect various surfaces and equipment. In these solutions, the concentration of the active chemical agent, the temperature of the solution, or other parameters can affect the cleaning and disinfecting properties of the fluid. Accordingly, ensuring that a fluid is appropriately formulated and prepared for an intended application can help ensure that the fluid provides suitable cleaning and disinfecting properties in subsequent use.

This disclosure describes an optical sensor for determining a characteristic of a fluid medium. In particular, this disclosure describes methods, systems, and apparatuses related to an optical sensor that may be used to determine a characteristic of a fluid medium. The optical sensor may be used to determine a plurality (e.g., two, three, or more) of characteristics of the fluid medium such as, e.g., the concentration of one, two, or more chemical species in the fluid medium, the temperature of the fluid medium, or the like. Depending on the application, the optical sensor may be implemented as an online sensor that receives a flow of fluid from a fluid source on a continuous or periodic basis and analyzes the fluid to determine the plurality of characteristics in substantially real-time. For example, the optical sensor may be connected to a flow of fluid via a pipe, tube, or other conduit. The optical sensor may then receive a sample of the fluid from the source via the conduit and analyze the fluid to determine the plurality of characteristics of the fluid.

In one example, the optical sensor is configured as a fluorometer that directs light into the fluid medium and detects fluorescent emissions emitted by the fluid medium. The optical sensor may include a sensor head that includes a light source to emit light into the fluid medium and a detector to detect fluorescent emissions from the fluid medium. The sensor head may also include a different type of sensor such as, e.g., a temperature sensor, for sensing a different type of characteristic of the fluid medium. When the sensor head is inserted into a flow chamber that is connected to a source of the fluid medium, the sensor head can be configured to determine multiple properties of the fluid.

In accordance with the techniques described in this disclosure, a flow chamber with an inlet for receiving a sample of the fluid medium and an outlet for discharging the sample of fluid medium is provided. The flow chamber may define a bounded cavity into which the sensor head can be inserted. In operation, the flow chamber may direct fluid past various sensor components of the sensor head in order to determine a characteristic of the fluid medium. For example, the flow chamber may be configured such that, when fluid enters the flow chamber, the fluid divides into at least a major stream passing adjacent (e.g., between) the light source and the detector of the sensor head and a minor stream passing adjacent another sensor of the sensor head. Depending on the configuration of the flow chamber and the sensor head, the flow chamber may split the fluid entering through the inlet into a major stream that passes substantially parallel to an elongated sensor housing and a minor stream that passes substantially orthogonally to a major axis of the elongated sensor housing.

By dividing an inlet fluid stream into a major stream and a minor stream, the flow chamber may direct fluid past multiple different sensors of the sensor head while preventing gas bubbles in the fluid from forming an air lock within the flow chamber. For example, when the fluid is a liquid fluid that includes dissolved or suspended air bubbles, the air bubbles may separate from the fluid within the flow chamber. While such air bubbles may not be problematic if the sensor is placed in a stationary pool of fluid or if the flow chamber has only a single fluid stream passing through the flow chamber, the air bubbles may create an airlock when the flow chamber divides into multiple different streams. However, by dividing the inlet fluid stream into a major stream and a minor stream, where the major stream is directed through a region where gas bubbles are likely to accumulate, the flow chamber may be configured to direct fluid past multiple different sensors while inhibiting the generation of an airlock. Depending on the configuration, the major stream may comprise a majority of the fluid entering the flow chamber (e.g., greater than or equal to 50 volume percent of the fluid entering the flow chamber) while the minor stream may comprise a minority of the fluid entering the flow chamber.

Example optical sensor and flow chambers will be described in greater detail below with respect to FIGS. 2-10. However, an example fluid system including an example optical sensor system will first be described with respect to FIG. 1.

FIG. 1 is a conceptual diagram illustrating an example fluid system 100, which may be used to produce a chemical solution having fluorescent properties. Fluid system 100 includes optical sensor 102, a reservoir 104, a controller 106, and a pump 108. Reservoir 104 may store a concentrated chemical agent that can be blended with a diluent, such as water, to generate the chemical solution. Optical sensor 102 is optically connected to fluid pathway 110 and is configured to determine one or more characteristics of the solution traveling through the fluid pathway. In operation, optical sensor 102 can communicate with controller 106, and controller 106 can control fluid system 100 based on the fluid characteristic information generated by the optical sensor.

Controller 106 is communicatively connected to optical sensor 102 and pump 108. Controller 106 includes processor 112 and memory 114. Controller 106 communicates with pump 108 via a connection 116. Signals generated by optical sensor 102 are communicated to controller 106 via a wired or wireless connection, which in the example of FIG. 1 is illustrated as wired connection 118. Memory 114 stores software for running controller 106 and may also store data generated or received by processor 112, e.g., from optical sensor 102. Processor 112 runs software stored in memory 114 to manage the operation of fluid system 100.

As described in greater detail below, optical sensor 102 includes a flow chamber and a sensor head inserted into the flow chamber. The sensor head may be configured to determine a plurality of characteristics of a fluid passing through the flow chamber such as, e.g., a concentration of a chemical compound in the fluid, the temperature of the fluid, or the like. In one example, the flow chamber defines a bounded cavity that includes a single fluid inlet and a single fluid outlet. The flow chamber may further define at a plurality of fluid channels (e.g., two, three, or more fluid channels) within the flow chamber that are configured to direct fluid adjacent a plurality of different sensors of the sensor head. For example, the flow chamber may define a major flow channel bounded between the flow chamber housing and a portion of the sensor head that includes a light source and a detector for detecting fluorescent emissions from a fluid flowing through the flow chamber. The flow chamber may also define a minor flow channel bounded between the flow chamber housing and a portion of the sensor head that includes another sensor, such as a temperature sensor for determining a temperature of the fluid flowing through the flow chamber.

In the example of FIG. 1, fluid system 100 is configured to generate a chemical solution having fluorescent properties. Fluid system 100 can combine one or more concentrated chemical agents stored within reservoir 104 with water or another diluting fluid to produce the chemical solutions. Example chemical solutions that may be produced by fluid system 100 include, but are not limited to, cleaning agents, sanitizing agents, cooling water for industrial cooling towers, biocides such as pesticides, anti-corrosion agents, anti-scaling agents, anti-fouling agent, laundry detergents, clean-in-place cleaners, floor coatings, vehicle care compositions, water care compositions, bottle washing compositions, and the like.

The chemical solutions generated by fluid system 100 may emit fluorescent radiation in response to optical energy directed into the solutions by optical sensor 102. Optical sensor 102 can then detect the emitted fluorescent radiation and determine various characteristics of the solution, such as a concentration of one or more chemical compounds in the solution, based on the magnitude of the emitted fluorescent radiation. In order to enable optical sensor 102 to detect fluorescent emissions, the fluid generated by fluid system 100 and received by optical sensor 102 may include a molecule that exhibits fluorescent characteristics. In some examples, the fluid may include a polycyclic compound and/or a benzene molecule that has one or more substituent electron donating groups such as, e.g., —OH, —$NH_2$, and —$OCH_3$, which may exhibit fluorescent characteristics. Depending on the application, these compounds may be naturally present in the chemical solutions generated by fluid system 100 because of the functional properties (e.g., cleaning and sanitizing properties) imparted to the solutions by the compounds.

In addition to or in lieu of a naturally fluorescing compound, the fluid generated by fluid system 100 and received by optical sensor 102 may include a fluorescent tracer (which may also be referred to as a fluorescent marker). The fluorescent tracer can be incorporated into the fluid specifically to impart fluorescing properties to the fluid. Example fluorescent tracer compounds include, but are not limited to naphthalene disulfonate (NDSA), 2-naphthalenesulfonic acid, Acid Yellow 7, 1,3,6,8-pyrenetetrasulfonic acid sodium salt, and fluorescein.

Independent of the specific composition of the fluid generated by fluid system 100, the system can generate fluid in any suitable fashion. Under the control of controller 106, pump 108 can mechanically pump a defined quantity of concentrated chemical agent out of reservoir 104 and combine the chemical agent with water to generate a liquid solution suitable for the intended application. Fluid pathway 110 can then convey the liquid solution to an intended discharge location. In some examples, fluid system 100 may generate a flow of liquid solution continuously for a period of time such as, e.g., a period of greater than 5 minutes, a period of greater than 30 minutes, or even a period of greater than 24 hours. Fluid system 100 may generate solution continuously in that the flow of solution passing through fluid pathway 110 may be substantially or entirely uninterrupted over the period of time.

In some examples, monitoring the characteristics of the fluid flowing through fluid pathway 110 can help ensure that the fluid is appropriately formulated for an intended downstream application. Monitoring the characteristics of the fluid flowing through fluid pathway 110 can also provide feedback information, e.g., for adjusting parameters used to generate new fluid solution. For these and other reasons, fluid system 100 can include a sensor to determine various characteristics of the fluid generated by the system.

In the example of FIG. 1, fluid system 100 includes optical sensor 102. Optical sensor 102 is configured to determine one or more characteristics of the fluid flowing through fluid pathway 110. Example characteristics include, but are not limited to, the concentration of one or more chemical compounds within fluid, the temperature of the fluid, the pH of the fluid, and/or other characteristics of the fluid may help ensure that the fluid is appropriately formulated for an intended application. Optical sensor 102 communicates detected characteristic information to controller 106 via connection 118.

In response to receiving the detected characteristic, processor 112 of controller 106 may compare the determined characteristic information to one or more thresholds stored in memory 114 such as one or more concentration thresholds. Based on the comparison, controller 106 may adjust fluid system 100, e.g., so that the detected characteristic matches a target value for the characteristic. In some examples, controller 106 starts and/or stops pump 108 or increases and/or decreases the rate of pump 108 to adjust the concentration of a chemical compound flowing through fluid pathway 110. Starting pump 108 or increasing the operating rate of pump 108 can increase the concentration of the chemical compound in the fluid. Stopping pump 108 or decreasing the operating rate of pump 108 can decrease the concentration of chemical compound in the fluid. Although not illustrated in the example fluid system 100 of FIG. 1, controller 106 may also be communicatively coupled to a heat exchanger, heater, and/or cooler to adjust the temperature of fluid flowing through fluid pathway 110 based on characteristic information received from optical sensor 102.

Optical sensor 102 may be implemented in a number of different ways in fluid system 100. In the example shown in FIG. 1, optical sensor 102 is positioned in-line with fluid pathway 110 to determine a characteristic of the fluid flowing through the fluid pathway. In other examples, a pipe, tube, or other conduit may be connected between fluid pathway 110 and a flow chamber of optical sensor 102. In such examples, the conduit can fluidly connect the flow chamber (e.g., an inlet of the flow chamber) of optical sensor 102 to fluid pathway 110. As fluid moves through fluid pathway 110, a portion of the fluid may enter the conduit and pass adjacent a sensor head positioned within the fluid chamber, thereby allowing optical sensor 102 to determine one or more characteristics of fluid flowing through the fluid pathway. When implemented to receive fluid directly from fluid pathway 110, optical sensor 102 may be characterized as an online optical sensor. After passing through the flow chamber, analyzed fluid may or may not be returned to fluid pathway 110, e.g., via another conduit connecting an outlet of the flow chamber to the fluid pathway.

In yet other examples, optical sensor 102 may be used to determine one or more characteristics of a stationary volume of fluid that does not flow through a flow chamber of the optical sensor. When optical sensor 102 includes a flow chamber with inlet and outlet ports (FIGS. 7-10), the inlet and outlet ports may be plugged to created a bounded cavity for holding a stationary (e.g., non-flowing) volume of fluid. A bounded flow chamber may be useful for calibrating optical sensor 102. During calibration, the flow chamber can be filled with a fluid having known characteristics (e.g., a known concentration of one or more chemical compounds, a known temperature), and optical sensor 102 can determine estimated characteristics of the calibration solution. The estimated characteristics determined by the optical sensor can be compared to the known characteristics (e.g., by controller 106) and used to calibrate optical sensor 102.

Fluid system 100 in the example of FIG. 1 also includes reservoir 104, pump 108, and fluid pathway 110. Reservoir 104 may be any type of container that stores a chemical agent for subsequent delivery including, e.g., a tank, a tote, a bottle, and a box. Reservoir 104 may store a liquid, a solid (e.g., powder), and/or a gas. Pump 108 may be any form of pumping mechanism that supplies fluid from reservoir 104. For example, pump 108 may comprise a peristaltic pump or other form of continuous pump, a positive-displacement pump, or any other type of pump appropriate for the particular application. In examples in which reservoir 104 stores a solid and/or a gas, pump 108 may be replaced with a different type of metering device configured to deliver the gas and/or solid chemical agent to an intended discharge location. Fluid pathway 110 in fluid system 100 may be any type of flexible or inflexible tubing, piping, or conduit.

Figure 2:
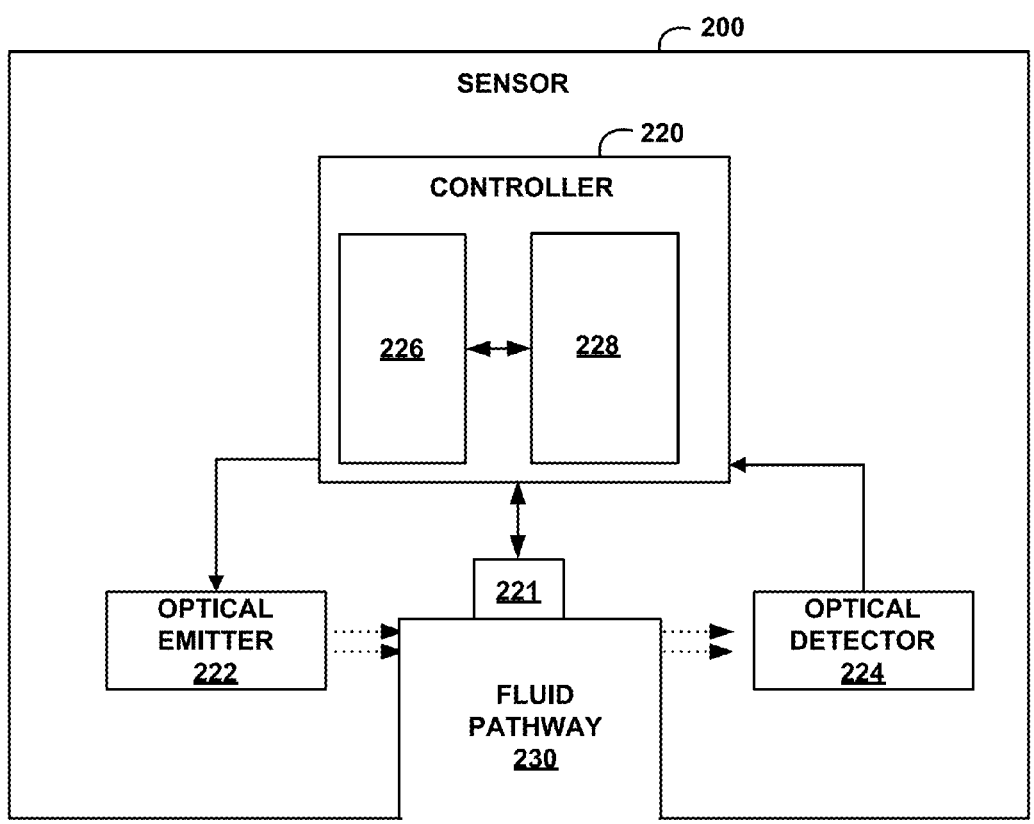
FIG. 2 is a block diagram illustrating an example optical sensor that may be used in the example fluid system of FIG. 1.

In the example of FIG. 1, optical sensor 102 determines a characteristic of the fluid flowing through fluid pathway 110 (e.g., concentration of a chemical compound, temperature or the like) and controller 106 controls fluid system 100 based on the determined characteristic and, e.g., a target characteristic stored in memory 109. FIG. 2 is block diagram illustrating an example of an optical sensor 200 that determines a characteristic of a fluid medium. Sensor 200 may be used as optical sensor 102 in fluid system 100, or sensor 200 may be used in other applications beyond fluid system 100.

With reference to FIG. 2, sensor 200 includes a controller 220, one or more optical emitters 222 (referred to herein as "optical emitter 222"), one or more optical detectors 224 (referred to herein as "optical detector 224"), and a temperature sensor 221. Controller 220 includes a processor 226 and a memory 228. In operation, optical emitter 222 directs light into fluid flowing through fluid channel 230 and optical detector 224 detects fluorescent emissions generated by the fluid. The light directed into the fluid by optical emitter 222 may generate fluorescent emissions by exciting electrons of fluorescing molecules within the fluid, causing the molecules to emit energy (i.e., fluoresce) that can be detected by optical detector 224. For example, optical emitter 222 may direct light at one frequency (e.g., ultraviolet frequency) into fluid flowing through fluid channel 230 and cause fluorescing molecules to emit light energy at a different frequency (e.g., visible light frequency). Temperature sensor 221 within sensor 200 can measure a temperature of fluid flow adjacent to (e.g., in contact with) the sensor. In some examples, sensor 200 communicates with external devices, such as controller 106 (FIG. 1).

Memory 228 stores software and data used or generated by controller 220. For example, memory 228 may store data used by controller 220 to determine a concentration of one or more chemical components within the fluid being monitored by sensor 200. In some examples, memory 228 stores data in the form of an equation that relates fluorescent emissions detected by optical detector 224 to a concentration of one or more chemical components.

Processor 226 runs software stored in memory 228 to perform functions attributed to sensor 200 and controller 220 in this disclosure. Components described as processors within controller 220, controller 106, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Optical emitter 222 includes at least one optical emitter that emits optical energy into a fluid present with fluid channel 230. In some examples, optical emitter 222 emits optical energy over range of wavelengths. In other examples, optical emitter 222 emits optical energy at one or more discrete wavelengths. For example, optical emitter 222 may emit at two, three, four or more discrete wavelengths.

In one example, optical emitter 222 emits light within the ultraviolet (UV) spectrum. Light within the UV spectrum may include wavelengths in the range from approximately 10 nm to approximately 400 nanometers. Light emitted by optical emitter 222 is directed into fluid within fluid channel 230. In response to receiving the optical energy, fluorescing molecules within the fluid may excite, causing the molecules to produce fluorescent emissions. The fluorescent emissions, which may or may not be at a different frequency than the energy emitted by optical emitter 222, may be generated as excited electrons within fluorescing molecules change energy states. The energy emitted by the fluorescing molecules may be detected by optical detector 224. For example, optical emitter 222 may emit light in the frequency range of approximately 280 nm to approximately 310 nm and, depending on the composition of the fluid, cause fluorescent emissions in the range of approximately 310 nm to approximately 400 nm.

Optical emitter 222 may be implemented in a variety of different ways within sensor 200. Optical emitter 222 may include one or more light sources to excite molecules within the fluid. Example light sources include light emitting diodes (LEDS), lasers, and lamps. In some examples, optical emitter 222 includes an optical filter to filter light emitted by the light source. The optical filter may be positioned between the light source and the fluid and be selected to pass light within a certain wavelength range. In some additional examples, the optical emitter includes a collimator, e.g., a collimating lens, hood or reflector, positioned adjacent the light source to collimate the light emitted from the light source. The collimator may reduce the divergence of the light emitted from the light source, reducing optical noise.

Sensor 200 also includes optical detector 224. Optical detector 224 includes at least one optical detector that detects fluorescent emissions emitted by excited molecules within fluid channel 230. In some examples, optical detector 224 is positioned on a different side of fluid channel 230 than optical emitter 222. For example, optical detector 224 may be positioned on a side of fluid channel 230 that is offset approximately 90 degrees relative to optical emitter 222. Such an arrangement may reduce the amount of light that is emitted optical emitter 222, transmitted through fluid within fluid channel 230, and detected by optical detector 224. This transmitted light can potentially cause interference with fluorescent emissions detected by the optical detector.

In operation, the amount of optical energy detected by optical detector 224 may depend on the contents of the fluid within fluid channel 230. If the fluid channel contains a fluid solution that has certain properties (e.g., a certain chemical compound and/or a certain concentration of a chemical species), optical detector 224 may detect a certain level of fluorescent energy emitted by the fluid. However, if the fluid solution has different properties (e.g., a different chemical compound and/or a different concentration of the chemical species), optical detector 224 may detect a different level of fluorescent energy emitted by the fluid. For example, if a fluid within fluid channel 230 has a first concentration of a fluorescing chemical compound(s), optical detector 224 may detect a first magnitude of fluorescent emissions. However, if the fluid within fluid channel 230 has second concentration of the fluorescing chemical compound(s) that is greater than the first concentration, optical detector 224 may detect a second magnitude of fluorescent emissions that is greater than the first magnitude.

Optical detector 224 may also be implemented in a variety of different ways within sensor 200. Optical detector 224 may include one or more photodetectors such as, e.g., photodiodes or photomultipliers, for converting optical signals into electrical signals. In some examples, optical detector 224 includes a lens positioned between the fluid and the photodetector for focusing and/or shaping optical energy received from the fluid.

Sensor 200 in the example of FIG. 2 also includes temperature sensor 221. Temperature sensor 221 is configured to sense a temperature of a fluid passing through a flow chamber of the sensor. In various examples, temperature sensor 316 may be a bi-metal mechanical temperature sensor, an electrical resistance temperature sensor, an optical temperature sensor, or any other suitable type of temperature sensor. Temperature sensor 221 can generate a signal that is representative of the magnitude of the sensed temperature.

Controller 220 controls the operation of optical emitter 222 and receives signals concerning the amount of light detected by optical detector 224. Controller 220 also received signals from temperature sensor 221 concerning the temperature of the fluid in contact with the sensor. In some examples, controller 220 further processes signals, e.g., to determine a concentration of more or more chemical species within the fluid passing through fluid channel 230.

In one example, controller 220 controls optical emitter 222 to direct radiation into a fluid and further controls optical detector 224 to detect fluorescent emissions emitted by the fluid. Controller 220 then processes the light detection information to determine a concentration of a chemical species in the fluid. For example, in instances in which a fluid includes a fluorescent tracer, a concentration of a chemical species of interest can be determined based on a determined concentration of the fluorescent tracer. Controller 220 can determine a concentration of the fluorescent tracer by comparing the magnitude of fluorescent emissions detected by optical detector 224 from a fluid having an unknown concentration of the tracer to the magnitude of the fluorescent emissions detected by optical detector 224 from a fluid having an known concentration of the tracer. Controller 220 can determine the concentration of a chemical species of interest using Equations (1) and (2) below:

$$C_c = C_m \times C_o / C_f \quad \text{Equation 1:}$$

$$C_m = K_m \times (S_x - Z_o) \quad \text{Equation 2:}$$

In Equations (1) and (2) above, $C_c$ is a current concentration of the chemical species of interest, $C_m$ is a current concentration of the fluorescent tracer, $C_o$ is a nominal concentration of the chemical species of interest, $C_f$ is a nominal concentration of the fluorescent tracer, $K_m$ is a slope correction coefficient, $S_x$ is a current fluorescent measurement signal, and $Z_o$ is a zero shift. Controller 220 may further adjust the determined concentration of the chemical species of interest based on the temperature measured by temperature sensor 221.

Figure 3:
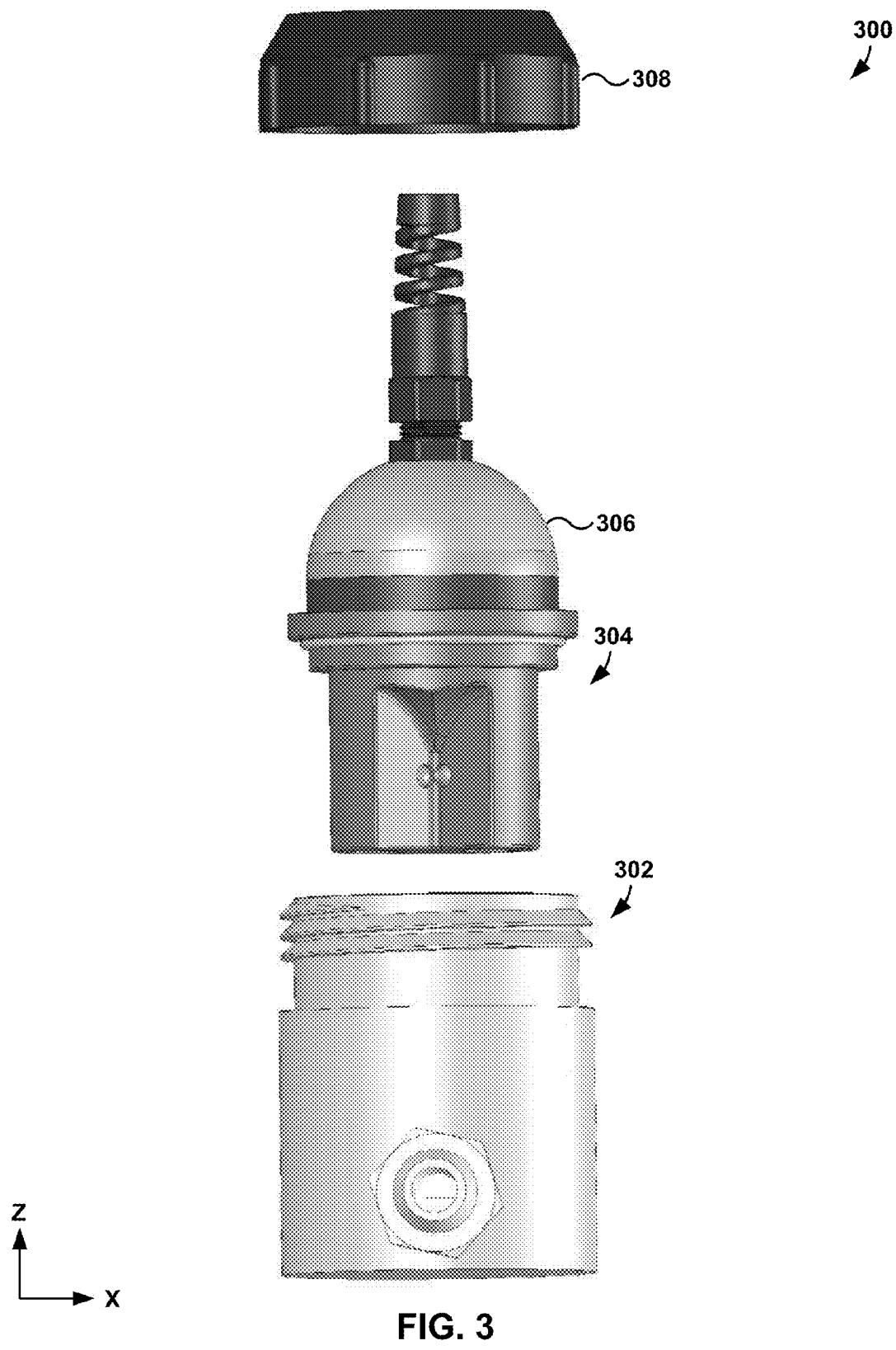
FIGS. 3 and 4 are schematic drawings of an example physical configuration of an optical sensor that may be used by the optical sensors in FIGS. 1 and 2.
Figure 4:
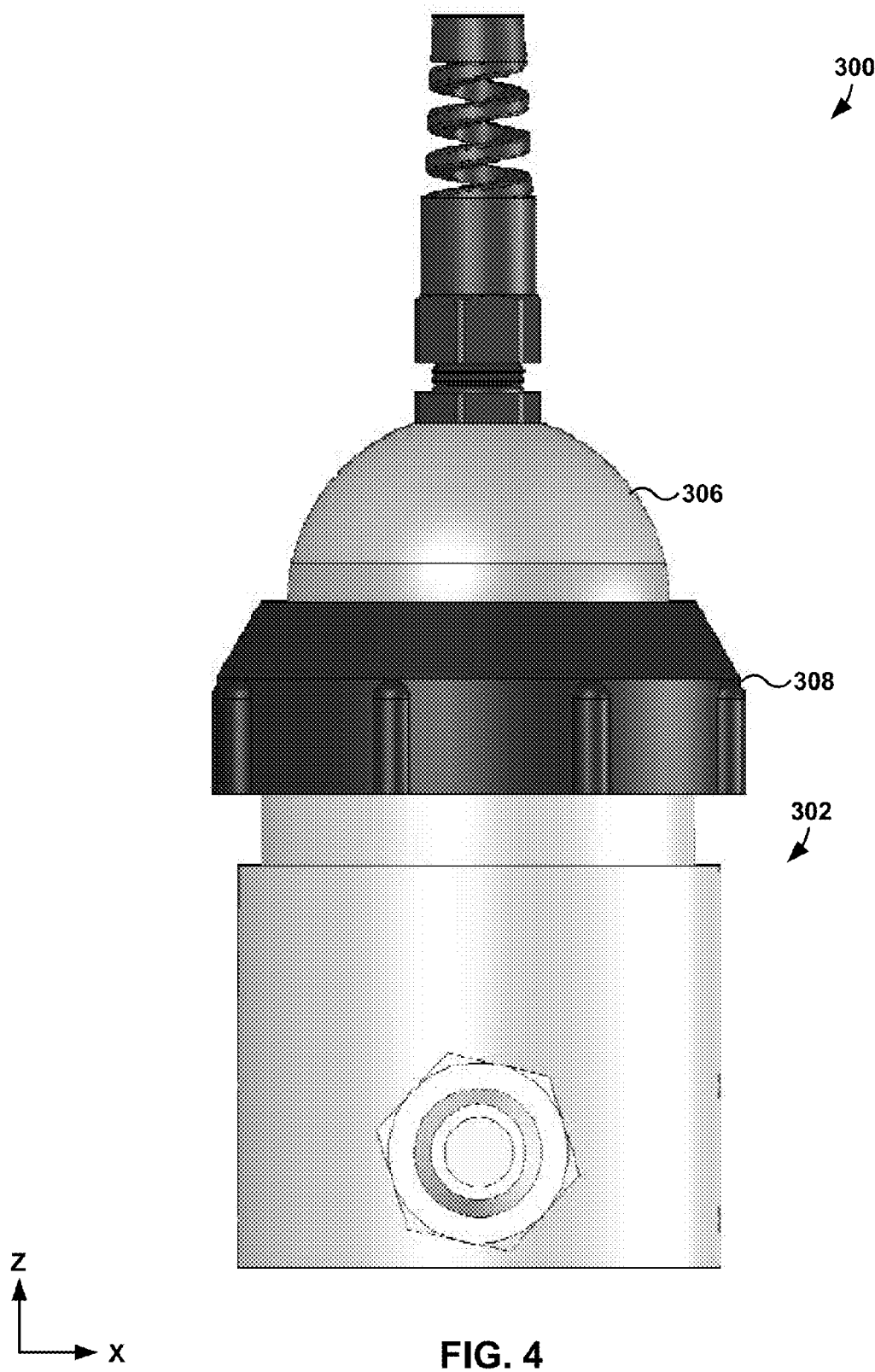

Sensor 102 (FIG. 1) and sensor 200 (FIG. 2) can have a number of different physical configurations. FIGS. 3 and 4 are schematic drawings of one example configuration of a sensor 300, which can be used by sensor 102 and sensor 200. Sensor 300 includes a flow chamber 302, a sensor head 304, a sensor cap 306, and a locking member 308. Sensor head 304 is shown outside of and insertable into flow chamber 302 in FIG. 3, while sensor head is shown inserted into flow chamber 302 and secured to the flow chamber via locking member 308 in FIG. 4. When sensor head 304 is inserted into and secured to flow chamber 302, the flow chamber may define a bounded cavity that receives fluids from a sample source (e.g., fluid system 100 in FIG. 1) and controls fluid flow past various sensor components of sensor head 304. For example, as described in greater detail below, flow chamber 302 may define at least two fluid flow channels that are configured to direct fluid past different sensory components of sensor head 304. The fluid flow channels may be designed to promote efficient operation of sensor 300 including, e.g., when the sensor is implemented as an online sensor continuously receiving moving fluid from a fluid source.

Flow chamber 302 of sensor 300 is configured to receive and contain sensor head 304. In general, sensor head 304 may be any component of sensor 300 that is insertable into flow chamber 302 and configured to sense a characteristic of a fluid within the fluid chamber. In various examples, sensor head 304 may be configured to sense characteristics for determining a concentration of one or more chemical compounds within the fluid in flow chamber 302, a temperature of the fluid in the fluid chamber, the pH of the fluid in the fluid chamber, and/or other characteristics of the fluid may help ensure that the fluid is appropriately formulated for an intended application, as described above with respect to FIGS. 1 and 2.

Figure 6:
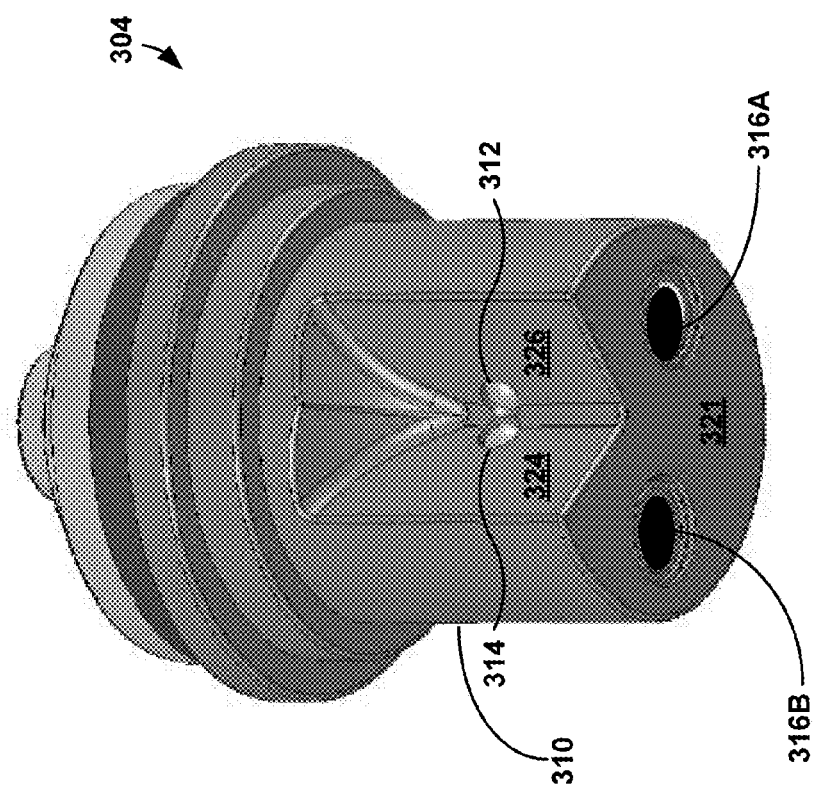
FIGS. 5 and 6 are alternative views of an example sensor head that may be used for the example optical sensor of FIGS. 3 and 4.
Figure 5:
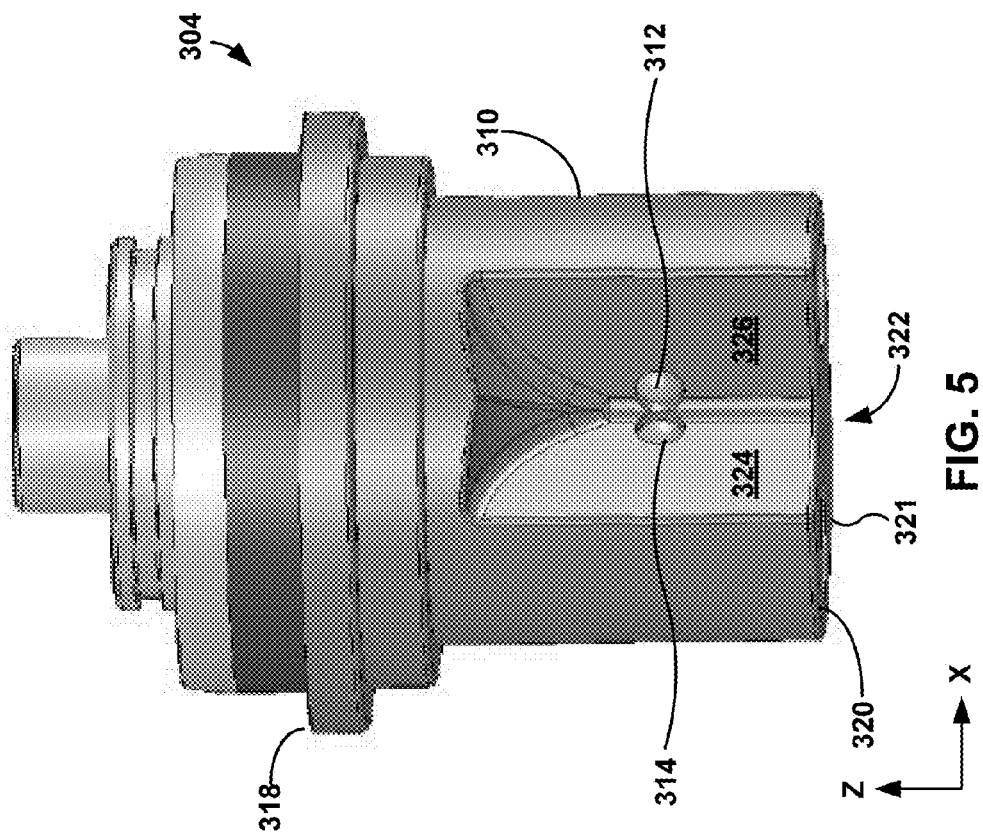

FIGS. 5 and 6 are alternative views of the example sensor head 304 illustrated in FIG. 3. As shown, sensor head 304 includes a sensor head housing 310, a first optical window 312, a second optical window 314, and at least one temperature sensor which, in the illustrated example, is shown as two temperature sensors 316A and 316B (collectively "temperature sensor 316"). Sensor head housing 310 defines a fluid impermeable structure that can house various components of sensor 300 such as, e.g., an optical emitter (FIG. 2) and an optical detector (FIG. 2). Sensor head housing 310 can be at least partially, and in some cases fully, immersed in a fluid. First optical window 312 defines an optically transparent section of sensor head housing 310 through which an optical emitter of sensor 300 can direct light into fluid within flow chamber 302, e.g., to cause fluorescent emissions. Second optical window 314 defines a different optically transparent section of sensor head housing 310 through which an optical detector of sensor 300 can receive fluorescent emissions emitted by the fluid within flow chamber 302. Temperature sensor 316 is configured to contact fluid within flow chamber 302 for determining a temperature of the fluid.

Sensor head housing 310 can define any suitable size and shape, and the size and shape of the sensor head housing can vary, e.g., depending on the number and arrangement of sensors carried by the housing. In the example of FIGS. 5 and 6, sensor head housing 310 defines an elongated body that extends from a proximal end 318 to a distal end 320 (i.e., in the Z-direction indicated on FIGS. 5 and 6) and includes a planar bottom surface 321. In some examples, sensor head housing 310 defines an elongated body that has a length in the Z-direction indicated on FIGS. 5 and 6 that is greater than a major width (e.g., in either X-direction or the Y-direction indicated on FIGS. 5 and 6). In other examples, sensor head housing 310 defines a length that is less than a major width of the housing.

While sensor head housing 310 is illustrated as defining a substantially circular cross-sectional shape (i.e., in the X-Y plane indicated on FIGS. 5 and 6), in other examples the housing can define other shapes. Sensor head housing 310 can define any polygonal (e.g., square, hexagonal) or arcuate (e.g., circular, elliptical) shape, or even combinations of polygonal and arcuate shapes. For instance, in some examples, sensor head housing 310 defines an angular cutout projecting towards an interior of the housing. The angular cutout may provide a location for positioning first optical window 312 and second optical window 314, e.g., to direct light from a light emitter through one window into a fluid sample and to receive fluorescent emissions generated by the fluid sample through another window. The angular cutout may also define a fluid channel for directing fluid between the first optical window and the second optical widow, e.g., when sensor head housing 310 is inserted into flow chamber 302 (FIG. 3) and fluid is flowing through the flow chamber.

In the example of sensor head housing 310, the housing includes an angular cutout 322 defined by a first planar surface 324 and a second planar surface 326. First planar surface 324 and second planar surface 326 each extend radially inwardly toward a center of sensor head housing 310. First planar surface 324 intersects second planar surface 326 to define an intersection angle between the two planar surfaces. In some examples, the intersection angle between first planar surface 324 and second planar surface 326 is approximately 90 degrees, although the intersection angle can be greater than 90 degrees or less than 90 degrees and it should be appreciated that a sensor in accordance with the disclosure is not limited in this respect.

When sensor head housing 310 includes angular cutout 322, first optical window 312 can be positioned on one side of the angular cutout while second optical window 314 can be positioned on a different side of the angular cutout. Such an arrangement may reduce the amount of light that is emitted an optical emitter, transmitted through fluid within flow chamber 302, and detected by an optical detector, e.g., as compared to if first optical window 312 is positioned 180 degrees across from second optical window 314. Light generated by an optical emitter that is transmitted through a fluid and detected by an optical detector can potentially interfere with the ability of the optical detector to detect fluorescent emissions.

First optical window 312 and second optical window 314 are optically transparent portions of sensor head housing 310. First optical window 312 may be optically transparent to a frequency of light emitted by an optical emitter of sensor 300. Second optical window 314 may be optically transparent to a frequency of fluorescent emissions emitted by a fluid within fluid chamber. In operation, first optical window 312 and second optical window 314 may provide optical pathways for transmitting light generated by an optical emitter housed within sensor head housing 310 into a fluid in flow chamber 302 and for receiving fluorescent emissions emitted by the fluid by an optical detector housed within the sensor head housing.

In some examples, first optical window 312 and second optical window 314 are fabricated from the same material while in other examples, first optical window 312 is fabricated from a material that is different than the material used to fabricate second optical window 314. First optical window 312 and/or second optical window 314 may or may not include a lens, prism, or other optical device that transmit and refracts light. For example, first optical window 312 and/or second optical window 314 may be defined by a ball lens positioned within an optical channel extending through sensor head housing 310. The ball lens can be fabricated from glass, sapphire, or other suitable optically transparent materials.

In the examples of FIGS. 5 and 6, sensor head housing 310 includes a first optical window 312 for transmitting light into a fluid and a second optical window 314 for receiving fluorescent emissions from the fluid. First optical window 312 is positioned at substantially the same position along the length of sensor head housing 310 as second optical window 314 (i.e., in the Z-direction indicated on FIGS. 5 and 6). During use, fluid within flow chamber 302 (FIG. 3) may move between an optical axis extending through a center of first optical window 312 and an optical axis extending through a center of second optical window 314, e.g., by flowing in the positive Z-direction indicated on FIGS. 5 and 6. As the fluid moves past the optical windows, a light emitter may transmit light through first optical window 312 and into the fluid, causing molecules in the fluid to excite and fluoresce. Before the fluorescing fluid flows past second optical window 314, optical energy emitted by the fluorescing molecules may be received through second optical window 314 by an optical detector.

Although first optical window 312 is positioned at substantially the same position along the length of sensor head housing 310 as second optical window 314 in the example of sensor head 304, in other examples, first optical window 312 may be offset along the length of the sensor head housing from second optical window 314. For example, second optical window 314 may be positioned closer to proximal end 318 of sensor head housing 310 than first optical window 312. In addition, although sensor head 304 is illustrated as including a single optical window for emitting optical energy and a single optical window for receiving optical energy, in other examples, sensor head 304 can include fewer optical windows (e.g., a single optical window) or more optical windows (e.g., three, four, or more), and the disclosure is not limited in this respect.

During operation, sensor 300 can detect fluorescent emissions from a fluid flowing through flow chamber 302. The fluorescent emission data may be used to determine a concentration of a chemical species flowing through the flow chamber or to determine other properties of the fluid in the flow chamber. Depending on the application, additional data about the characteristics of the fluid flowing through flow chamber 302 beyond what can be obtained by fluorometric detection may be useful to monitor and/or adjust the properties of the fluid. For this reason, sensor 300 may include a different sensor in addition to a fluorometric optical sensor for sensing different properties of the fluid in flow chamber 302.

In the FIGS. 5 and 6, sensor head 304 includes temperature sensor 316 for measuring a temperature of fluid in flow chamber 302. Temperature sensor 316 can sense a temperature of the fluid and generate a signal corresponding to the sensed temperature. When configured with a temperature sensor, the temperature sensor can be implemented as a contact sensor that determines the temperature of a fluid by physically contacting the fluid or as a non-contact sensor that determines the temperature of the fluid without having the sensor physically contact the fluid.

In the example of sensor head 304, temperature sensor 316 is positioned on a different surface of sensor head housing 310 than optical windows 312, 314. Specifically, temperature sensor 316 is positioned on a bottom surface 321 of sensor head housing 310 while first optical windows 312 and second optical window 314 are positioned on a sidewall of the housing. In different examples, temperature sensor 316 may be flush with a surface (e.g., bottom surface 321) of sensor head housing 310, project outwardly from the surface of the sensor head housing, or be recessed relative to the surface of the sensor head housing.

Independent of the specific arrangement of temperature sensor 316 relative to sensor head housing 310, fluid within flow chamber 302 may flow adjacent the temperature sensor during operation of sensor 300. Fluid may flow adjacent temperature sensor 316 by flowing past and, optionally, in contact with, the temperature sensor so that the temperature sensor can sense a temperature of the fluid. For example, during operation of sensor 300, fluid may flow past temperature sensor 316 in the X- and/or Y-direction indicated on FIGS. 5 and 6, allowing the temperature sensor to sense a temperature of the moving fluid.

As briefly described above, sensor 300 (FIG. 3) includes flow chamber 302. flow chamber 302 is configured to receive and contain sensor head 304. In particular, in the example of FIG. 3, flow chamber 302 is configured to receive sensor head 304 by moving the sensor head in the negative Z-direction shown on FIG. 3 until a surface of the sensor head abuts a surface of the fluid chamber. The abutting surface may be bottom surface 321 of sensor head housing 310 (FIGS. 5 and 6) or a different surface of the sensor head. Once suitably positioned within flow chamber 302, locking member 308 can be secured over flow chamber 302 and sensor head 304 to mechanical affix the sensor head to the flow chamber.

Figure 7:
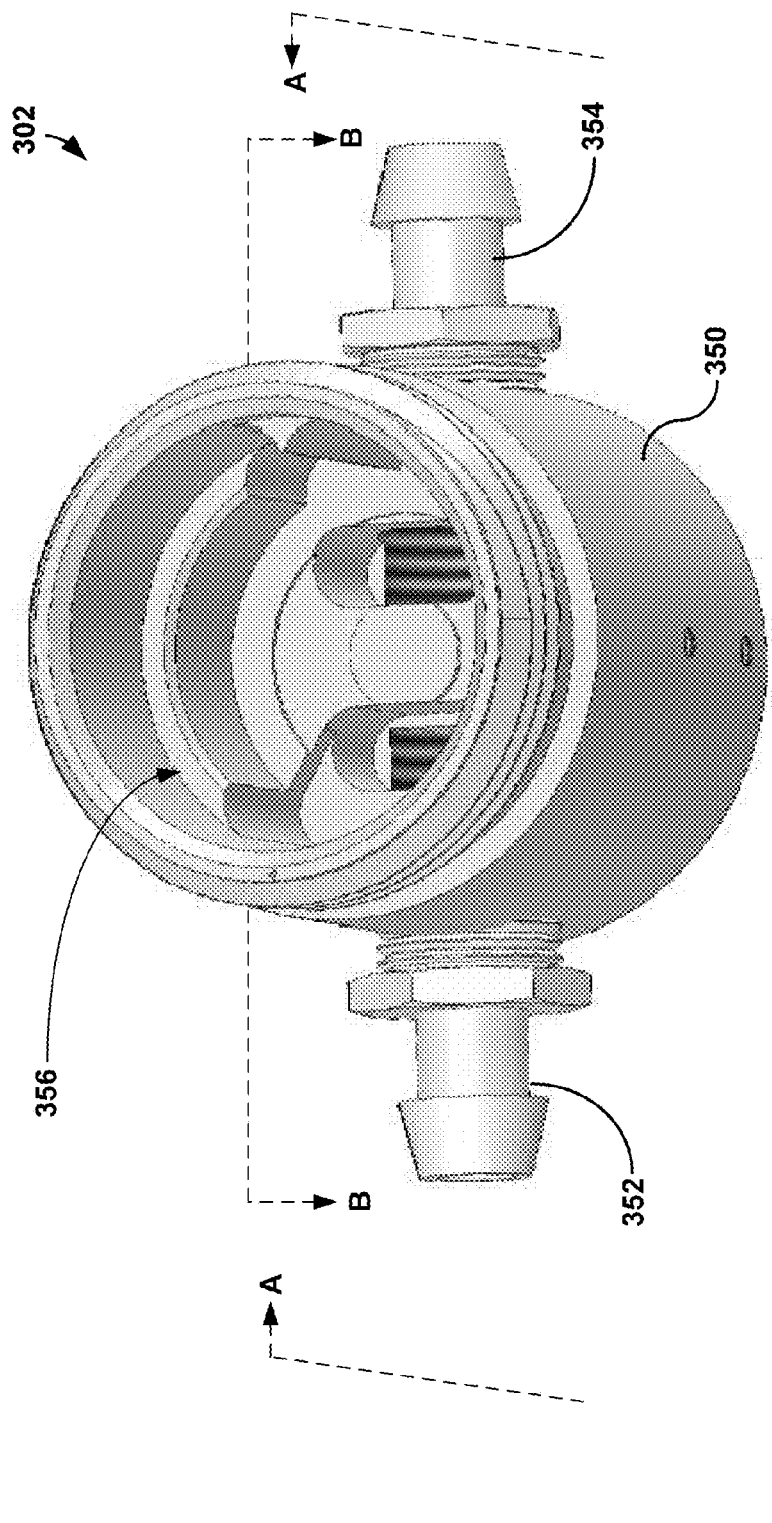
FIGS. 7-9 are different views of an example flow chamber that may be used for the example optical sensor of FIGS. 3 and 4.
Figure 8:
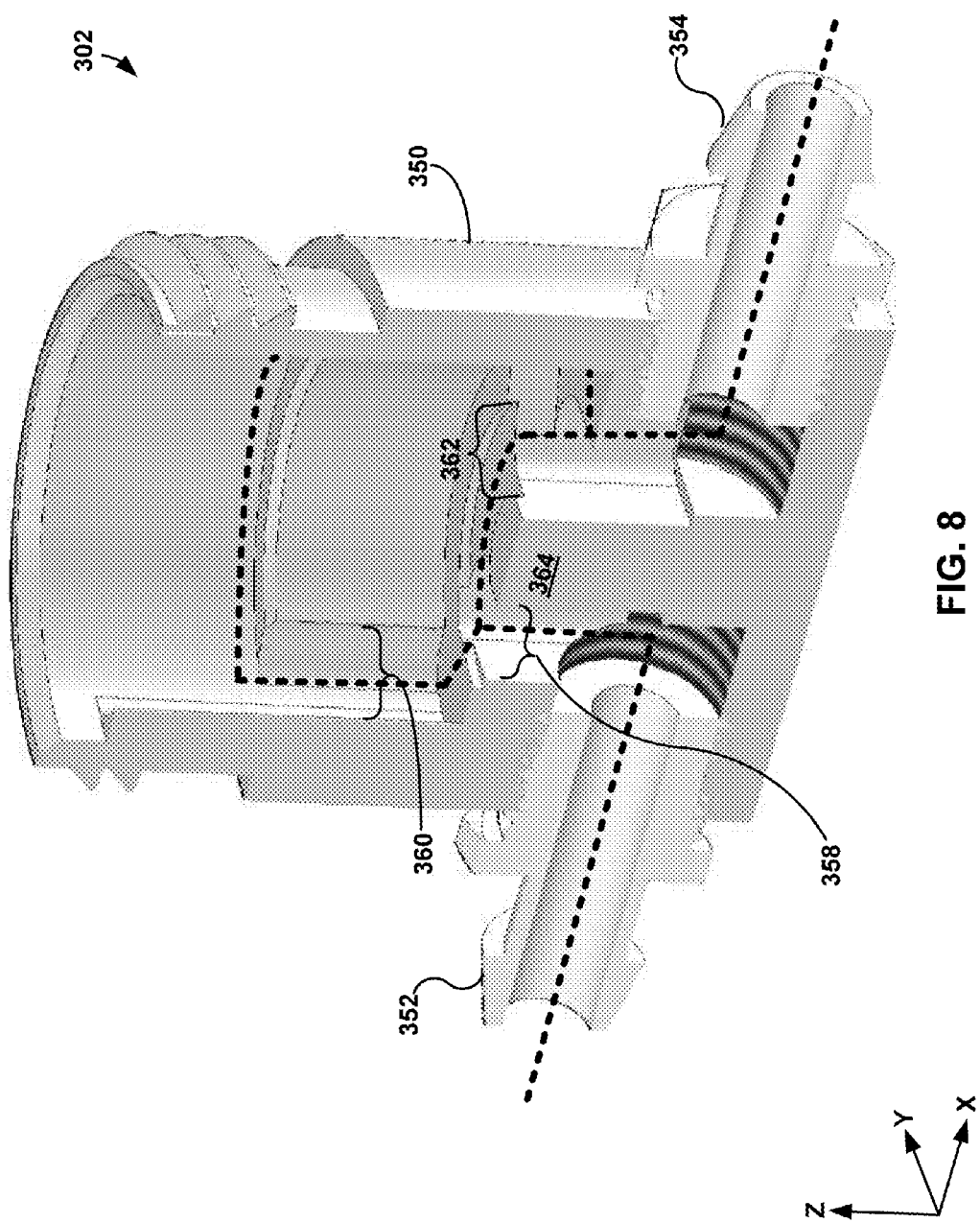
Figure 9:
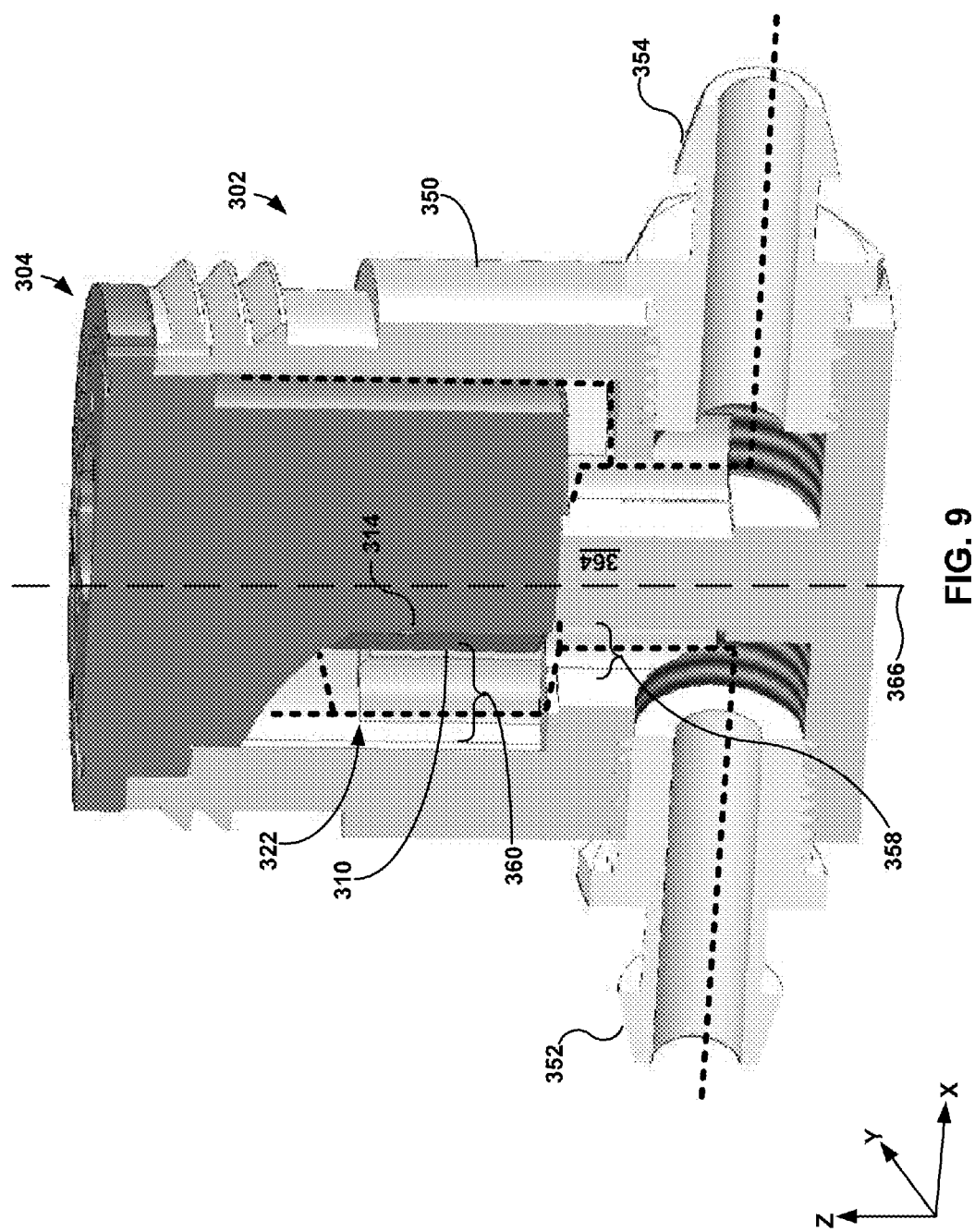

FIGS. 7-9 show different views of an example configuration of flow chamber 302. FIG. 7 is perspective top view of flow chamber 302 shown with sensor head 304 removed from the chamber. FIG. 8 is a cross-sectional side view of the flow chamber taken along the A-A cross-section line indicated on FIG. 7. FIG. 9 illustrates the cross-sectional side view of FIG. 8 with sensor head 304 inserted into the chamber.

In the illustrated example, flow chamber 302 includes a flow chamber housing 350, an inlet port 352, and an outlet port 354. Flow chamber housing 350 defines a cavity 356 that is configured (e.g., sized and shaped) to receive sensor head 304. Inlet port 352 extends through flow chamber housing 302 (e.g., a side wall of the housing) and is configured to convey fluid from outside of the housing to an interior of the housing. Outlet port 354 extends through flow chamber housing 302 (e.g., a side wall of the housing) and is configured to convey fluid from an interior of the housing to back outside of the housing. In operation, fluid may enter flow chamber 302 via inlet port 352, pass adjacent first optical window 312, second optical window 314, and temperature sensor 316 of sensor head 304, and discharge from the flow chamber via outlet port 354. When flow chamber 302 is used in online applications, fluid may flow through the chamber continuously for a period of time. For example, depending on the size and configuration of flow chamber 302, fluid may flow through the chamber at a rate ranging from 0.1 gallons per minute to 10 gallons per minute, although other flow rates are both possible and contemplated.

When sensor head 304 is inserted into flow chamber 302, the flow chamber may define a bounded cavity that can receive and contain fluid for analysis by sensor head 304. For example, flow chamber 302 may define fluid paths or channels that limit movement of fluid through the flow chamber to certain defined areas of the chamber. In some examples, the fluid channels may preferentially direct fluid toward optical windows 312, 314 and/or temperature sensor 316 of sensor head 304, which may help the sensor head to detect characteristics of the fluid.

Controlling fluid movement through flow chamber 302 may be useful to help ensure that fluid passes adjacent optical windows 312, 314 and temperature sensor 316 in such a way that the sensor components of sensor head 304 can adequately detect the characteristics of the fluid. When flow chamber 302 receives fluid continuously, e.g., from a downstream industrial process, the fluid may contain fouling materials (e.g., solid particles) and/or gas bubbles. These fouling materials and/or gas bubbles may accumulate within the flow chamber, inhibiting sensor head 304 from adequately detecting the characteristics of the fluid.

In some examples, bounding fluid movement through flow chamber 302 into defined flow channels can help prevent the accumulation of fouling materials and gas bubbles, e.g., by flushing accumulated fouling materials and gas bubbles out of the chamber. Bounding fluid movement through flow chamber 302 into defined fluid channels may also help ensure that fluid will pass adjacent the sensor components of sensor head 304 in such a way that the sensor components can detect characteristics of the fluid.

When sensor head 304 is inserted into flow chamber 302 in the example of FIGS. 8 and 9, the flow chamber defines an inlet fluid channel 358 that divides into a first fluid channel 360 and a second fluid channel 362. Inlet fluid channel 358 receives fluid from inlet port 352 and directs the fluid within cavity 356 of flow chamber 302. Inlet fluid channel 358 divides into first fluid channel 360 and second fluid channel 362. First fluid channel 360 extends adjacent first optical window 312 and second optical window 314 of sensor head 304. Second fluid channel 362 extends adjacent temperature sensor 316 of sensor head 304. In operation, fluid enters flow chamber 302 via inlet port 352 and is conveyed through inlet fluid channel 358. From inlet fluid channel 358, the fluid splits into first fluid channel 360 and second fluid channel 362. Fluid within first fluid channel 360 can be fluorometrically analyzed by an optical emitter and optical detector, e.g., positioned within sensor head 304, while the temperature of the fluid within second fluid channel 362 can be determined by temperature sensor 316 of sensor head 304.

When fluid is not flowing through flow chamber 302, first fluid channel 360 and second fluid channel 362 may be gaseous spaces bounded between portions of flow chamber housing 350 and sensor head housing 310. In some examples, flow chamber housing 350 and sensor head housing 310, in combination, limit vertical movement of fluid through the flow chamber (e.g., in the Z-direction indicated on FIGS. 8 and 9) and/or movement of fluid about the perimeter of sensor head 304 positioned within the flow chamber. For instance, in the example of FIG. 9, first fluid channel 360 is defined as a space between angular cutout 322 (FIGS. 4 and 5) of sensor head housing 310 and an interior wall of flow chamber housing 350. The sidewall(s) of sensor head housing 310 extending on either side of angular cutout 322 (e.g., about a perimeter of the sensor head housing) may be flush to and/or in contact with a corresponding sidewall of flow chamber housing 350. Such a configuration may substantially prevent fluid flowing through angular cutout 322 (e.g., in the positive Z-direction indicated on FIG. 9) from flowing around the perimeter of sensor head housing 310, rather than past first optical window 312 and second optical window 314 of the housing.

In the example of FIG. 9, second fluid channel 362 is defined as a space between a portion of bottom surface 321 of sensor head housing 310 and a bottom wall of flow chamber housing 350. Bottom surface 321 may bound second fluid channel 362 in the positive Z-direction indicated on FIGS. 8 and 9 while the bottom wall of flow chamber housing 350 may bound the fluid channel in the negative Z-direction. When so configured, fluid flow through second fluid channel 362 may be limited to the X-Y plane between bottom surface 321 and the bottom wall of flow chamber housing 350.

First fluid channel 360 and second fluid channel 362 can have any suitable size, and the size of the fluid channels can vary, e.g., depending on the anticipated flow rates through flow chamber 302. In some examples, first fluid channel 360 defines a size that is different than the size of second fluid channel 362. For example, first fluid channel 360 may define a flow volume (e.g., cross-sectional area per unit of length) that is greater than the flow volume of second fluid channel 362. When first fluid channel 360 defines a larger flow volume then second fluid channel 362, more fluid may pass through the first fluid channel per unit of time than second fluid channel. For example, in operation, a major portion (e.g., major volume) of fluid entering flow chamber 302 via inlet port 352 may pass through first fluid channel 360 while a minor portion (e.g., minor volume) of the fluid passes through second fluid channel 362.

Although first fluid channel 360 can be configured to carry any suitable amount of the fluid entering flow chamber 302 via inlet port 352, in some examples, sizing first fluid channel 360 to receive and carry a major portion of the fluid entering the flow chamber and sizing second fluid channel 362 to receive and carry a minor portion of the fluid may be useful to ensure that fluid adequately flows past the sensory components of sensor head 304. As noted above, when flow chamber 302 is used in online applications, the fluid chamber may receive fluid that includes fouling materials and/or gas bubbles. Depending on the configuration of flow chamber 302, the fouling materials and/or gas bubbles in the fluid may accumulate within the flow chamber during operation. For example, if first fluid channel 360 and second fluid channel 362 have the same flow volume and the fluid chamber is oriented so that fluid flowing through first fluid channel 360 (e.g., in the positive Z-direction indicated on FIGS. 8 and 9) flows against the force of gravity, gas bubbles in the fluid may accumulate within the first fluid channel. Accumulating gas bubbles may generate an airlock that prevents fluid movement through first fluid channel 360, forcing fluid entering flow chamber 302 to flow through second fluid channel 362. If fluid does not adequately flow through first fluid channel 360, sensor head 304 may not be able to accurately fluorometrically analyze the fluid in the flow chamber.

In some examples, configuring first fluid channel 360 to have a larger flow volume than second fluid channel 362 may reduce or eliminate the accumulation of fouling materials and/or gas bubbles in either of the channels. For example, sizing first fluid channel 360 to receive a major portion of the fluid entering flow chamber 302 via inlet port 352 and sizing second fluid channel 362 to receive a minor portion of the fluid entering the flow chamber may allow fluid flowing through the first channel to flush any accumulated fouling materials and/or gas bubbles out of the first channel. Depending on the configuration, first fluid channel 360 may be sized so greater than or equal to 50 volume percent of the fluid entering flow chamber 302 via inlet port 352 flows through the channel while less than 50 volume percent of the fluid flows through second fluid channel 362. For example, first fluid channel 360 may be sized so that greater 65 volume percent, greater than 85 volume percent, or greater than approximately 90 volume percent of the fluid entering flow chamber 302 flows through the channel. In such examples, second fluid channel 362 may be sized so that less than 35 volume percent, less than 15 volume percent, or less than approximately 10 volume percent of the fluid entering flow chamber 302 flows through the channel.

Independent of the specific size of the fluid channels in flow chamber 302, the number and arrangement of the fluid channels defined by the chamber may vary, e.g., depending the configuration of sensor head housing 310. Thus, while flow chamber 302 is described with respect to FIGS. 8 and 9 as defining first fluid channel 360 and second fluid channel 362, the flow chamber may define fewer fluid channels (e.g., one fluid channel) or more fluid channels (e.g., three, four, or more fluid channels) and the disclosure is not limited in this respect.

Figure 10:
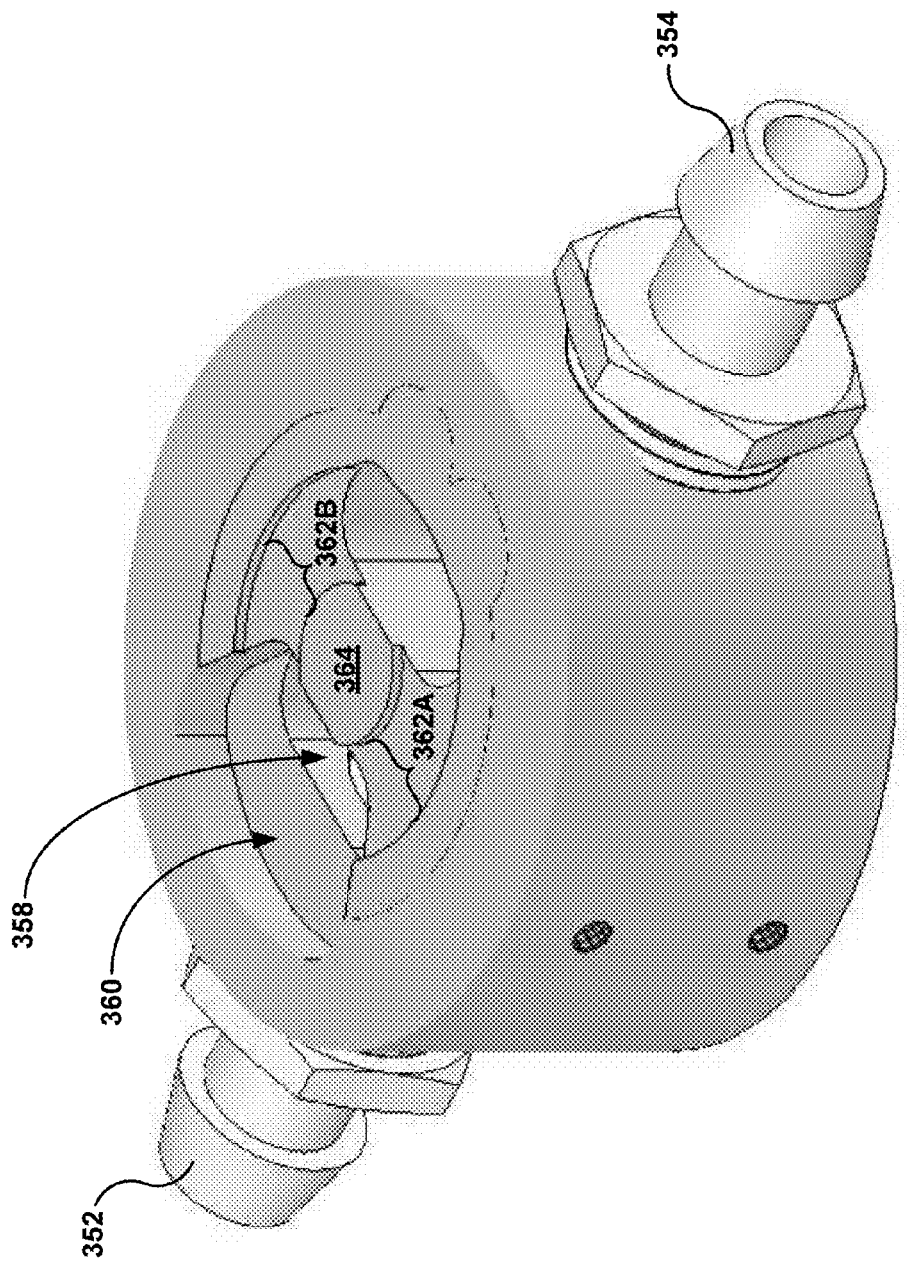
FIG. 10 is a cross-sectional view of the example flow chamber of FIG. 7.

FIG. 10 is a cross-sectional view of flow chamber 302 taken along the B-B cross-sectional line indicated on FIG. 7. In this example, flow chamber 302 includes inlet port 352, outlet port 354, inlet fluid channel 358, and first fluid channel 360. Flow chamber 302 in the example of FIG. 10 also includes second fluid channel 362, which is comprised of a first portion 362A and a second portion 362B. First portion 362A of second fluid channel 362 is separated from second portion 362B by a support member 364. In some examples, a portion of bottom surface 321 of sensor head housing 310 (FIGS. 5 and 6) is in contact with and supported by support member 364 when sensor head 304 is inserted into flow chamber 302. In operation, fluid enters flow chamber 302 via inlet port 352 and is conveyed through inlet fluid channel 358. From inlet fluid channel 358, the fluid splits into first fluid channel 360 and second fluid channel 362. Fluid entering second fluid channel 362 is further divided into first portion 362A of second fluid channel 362 and second portion 362B. Fluid within first portion 362A of second fluid channel 362 may flow adjacent temperature sensor 316A of sensor head 304 (FIGS. 5 and 6), while fluid within second portion 362B of second fluid channel 362 may flow adjacent temperature sensor 316B of the sensor head. In some examples, first portion 362A and second portion 362B of second fluid channel 362 each define the same flow volume, which may or may not be equal to one half the total flow volume of second fluid channel 362.

With further reference to FIGS. 8 and 9, fluid channels defined between flow chamber 302 and sensor head 304 of sensor 300 can have a variety of different orientations. Moreover, the orientations can vary, e.g., depending on the configuration of sensor head 304. In some examples, sensor head housing 310 of sensor head 304 defines an elongated body that extends from a proximal end to a distal end. In such examples, flow chamber housing 350 may define an elongated cavity 356 that is configured (e.g., sized and shaped) to receive the elongated sensor head housing. The elongated flow chamber housing may define a major axis extending through the length of the housing, which is illustrated as axis 366 extending in the Z-direction in FIG. 8. When fluid is moving through flow chamber 302 in such examples, the fluid may travel parallel to axis 366 as the fluid proceeds through inlet fluid channel 358. From inlet fluid channel 358, a major portion of the fluid may continue flowing parallel to axis 366 via first fluid channel 360, while a minor portion of the fluid may flow substantially orthogonally to axis 366 via second fluid channel 362.

After a fluid sample has flowed past the sensor components of sensor head 304, the fluid may be discharged from flow chamber 302 to allow a fresh fluid sample to enter the flow chamber. For this reason, flow chamber 302 may include an outlet for discharging analyzed fluid from the chamber. In some examples, flow chamber 302 defines a plurality of outlets for separately discharging fluid flowing through different fluid channels of the chamber. For example, flow chamber 302 may include a first fluid outlet for discharging fluid flowing through first fluid channel 360 and a second fluid outlet for discharging fluid flowing through second fluid channel 362. In other examples, flow chamber 302 defines a single fluid outlet for discharging a combined flow of fluid from multiple different fluid channels.

In the example of FIGS. 8 and 9, flow chamber 302 includes a single fluid outlet port 354. After flowing past first optical window 312 and second optical window 314, fluid in first fluid channel 360 is recombined with fluid that has flowed past temperature sensor 316 via second fluid channel 362. The recombined fluid stream is discharged from flow chamber 302 through outlet port 354. The flow exiting flow chamber 302 via outlet port 354 may be the same as the flow entering the flow chamber via inlet port 352.

Fluid moving through first fluid channel 360 can recombine with fluid moving through second fluid channel 362 in a variety of different ways. In the example of FIGS. 8 and 9, first fluid channel 360 directs fluid about a perimeter of flow chamber 302 to recombine fluid from the first fluid channel with fluid from second fluid channel 362. In particular, first fluid channel 360 extends parallel to the major length of sensor head 304 (e.g., in the Z-direction indicated on FIGS. 8 and 9) until the fluid channel extends past first optical window 312 and second optical window 314. Thereafter, first fluid channel 360 changes directions from extending parallel to the major length of sensor head 304 to extending substantially orthogonally to the major length of the sensor head. Specifically, first fluid channel 360 changes direction to extend about a perimeter of flow chamber 302 (e.g., between sensor head housing 310 and flow chamber housing 350). After traveling about the perimeter of flow chamber 302 (e.g., approximately 180 degrees about the perimeter of the flow chamber), first fluid channel 360 recombines with second fluid channel 362.

To define the discharge portion of first fluid channel 360, flow chamber housing 350 may have a larger internal cross-sectional area (e.g., in the X-Y plane indicated on FIGS. 8 and 9) at a first distance along the length of the flow chamber (e.g., in the Z-direction indicated on FIGS. 8 and 9) than at a second distance along the length of the flow chamber. When so configured, the sidewall(s) of sensor head housing 310 extending adjacent the portion of flow chamber housing 350 defining the larger internal cross-sectional area may not be flush to and/or in contact with fluid chamber housing. Rather, the sidewall(s) of sensor head housing 310 may be spaced from flow chamber housing 350 in the enlarged region of the fluid chamber housing to define the discharge portion of first fluid channel 360.

In some examples, first fluid channel 360 extends only in one direction (e.g., clockwise or counter-clockwise) about a perimeter of flow chamber 302 before recombining with second fluid chamber 362. In other examples, first fluid channel 360 extends in two directions (e.g., clockwise and counter-clockwise) about a perimeter of flow chamber 302 before recombining with second fluid chamber 362. For example, after extending parallel to the major length of sensor head 304, first fluid channel 360 may change direction and split into a first discharge portion that extends in one direction about a perimeter of flow chamber 302 and a second discharge portion that extends in an opposite direction about the perimeter of the flow chamber. The first discharge portion and the second discharge portion may or may not be sized to convey the same volume of fluid. Accordingly, while the cross-sectional illustrations of FIGS. 8 and 9 only illustrate one-half of sensor 300 with first fluid channel 360 including one discharge portion, the non-illustrated half of sensor 300 may appear substantially identical to FIGS. 8 and 9 and may include a second discharge portion. Dividing first fluid channel 360 into a first discharge portion and a second discharge portion may allow the length of flow chamber 302 to be reduced, providing a more compact flow chamber.

As briefly discussed above with respect to FIG. 7, flow chamber 302 includes an inlet port 352 and an outlet port 354. Inlet port 352 is configured to connect to a conduit for conveying fluid from a source (e.g., fluid system 100 in FIG. 1) to an interior of flow chamber 302. Outlet port 354 is configured to connect to a conduit for conveying fluid away from flow chamber 302. Inlet port 352 and outlet port 354 can be positioned at any suitable location about the perimeter of flow chamber housing 350. In the example of FIGS. 7-9, inlet port 352 is positioned approximately 180 degrees (e.g., on an opposite side) of the housing from outlet port 354. When so configured, flow chamber 302 may easily be installed in-line with other piping. That being said, inlet port 352 may be arranged at other locations relative to outlet port 354 and the disclosure is not limited in this respect.

With further reference to FIG. 3, sensor 300 also includes sensor cap 306 and locking member 308. Sensor cap 306 may define a cap that houses various electrical components of sensor 300. For example, sensor cap 306 may house at least a portion of an optical emitter (e.g., optical emitter 222) and/or an optical detector (e.g., optical detector 224) and/or a controller (e.g., controller 220) of sensor 300. Sensor cap 306 may be permanently affixed to (e.g., integrally molded with) sensor 300 or may be removable from sensor 300.

In some examples, sensor 300 does not include a controller and/or other electronic components that are physical housed with the sensor (e.g., in sensor cap 306). Rather, various components of sensor 300 may be located in one or more housings that are physically separate from the sensor and communicatively coupled to the sensor (e.g., via a wired or wireless connection). In one example, sensor cap 306 of sensor 300 is removable and sensor head 304 of the sensor is configured to connect to a handheld controller module. Example handheld controller modules that may be used with sensor 300 are described in US Patent Publication No. 2011/0240887, filed Mar. 31, 2010, and US Patent Publication No. 2011/0242539, also filed Mar. 31, 2010. The entire contents of these patent publications are incorporated herein by reference.

During operation, pressurized fluid may flow through fluid chamber 302 of sensor 300. When sensor head 304 is designed to be removable from fluid chamber 302, the pressurized fluid flowing through the flow chamber may try to force the sensor head out of the fluid chamber. For this reason, sensor 300 may include a locking member to lock sensor head 304 into flow chamber 302.

In the example of FIG. 3, sensor 300 includes locking member 308. Locking member 308 may help prevent sensor head 304 from disengaging with flow chamber 302 when pressurized fluid is flowing through the flow chamber. In some examples, locking member 308 is configured to secure sensor head 304 to flow chamber 302 by screwing the locking member over a portion of both the sensor head and the flow chamber. In different examples, locking member 308 may be configured to secure to sensor head 304 to flow chamber 302 using a different type of attachment feature such as, e.g., clips, bolts, or the like. By mechanically affixing sensor head 304 to fluid chamber 302, sensor 300 may define fluid-tight cavity (e.g., except for inlet port 352 and outlet port 354) for receiving and analyzing a fluid sample.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a non-transitory computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A fluorescence analysis system comprising:
a sensor head that includes at least one light source configured to emit light into a flow of fluid, at least one detector configured to detect fluorescent emissions from the flow of fluid, and a temperature sensor configured to sense a temperature of the flow of fluid; and
a flow chamber that includes a housing defining a cavity into which the sensor head is inserted, an inlet port extending through the housing and configured to communicate the flow of fluid from outside of the cavity to an interior of the cavity, and an outlet port extending through the housing and configured to communicate the flow of fluid from the interior of the cavity to back outside of the cavity,
wherein the housing is configured such that, when the flow of fluid enters the housing via the inlet port, the flow of fluid divides into at least a major stream passing through a first physical channel adjacent the light source and the detector and a minor stream passing through a second physical channel adjacent the temperature sensor, the first physical channel being different than the second physical channel.

2. The fluorescence analysis system of claim 1, wherein sensor head includes an elongated sensor housing extending from a proximal end to a distal end, the temperature sensor is positioned at the distal end of the elongated sensor housing, and the light source and the detector are positioned between the proximal end and the distal end of the elongated sensor housing, and
wherein the housing is configured such that, when the flow of fluid enters the housing via the inlet port, the major stream passes substantially parallel to the elongated sensor housing and the minor stream passes substantially orthogonally to a major axis of the elongated sensor housing.

3. The fluorescence analysis system of claim 1, wherein the housing is configured such that, when the flow of fluid enters the housing via the inlet port, less than 15 volume percent of the flow of fluid entering the cavity divides toward the minor stream.

4. The fluorescence analysis system of claim 1, wherein the housing defines a major axis and the housing is configured such that, when the flow of fluid enters the housing via the inlet port, the flow of fluid travels parallel to the major axis, the minor stream divides from the flow of fluid in a direction substantially orthogonal to the major axis, and the major stream is defined as a portion of the flow of fluid that continues past where the minor stream divides from the flow of fluid.

5. The fluorescence analysis system of claim 4, wherein the housing is oriented so that the flow of fluid travels upward against a force of gravity and the minor stream divides from the flow of fluid in a direction substantially orthogonal to the direction of the force of gravity.

6. The fluorescence analysis system of claim 4, wherein the outlet port is positioned approximately opposite the inlet port, and the housing is configured such that, when the flow of fluid enters the housing via the inlet port, the major stream and the minor stream recombine within the cavity and discharge through the outlet port.

7. The fluorescence analysis system of claim 4, wherein the housing is configured such that, when the flow of fluid enters the housing via the inlet port, the major stream divides after passing the light source and detector into a first discharge stream that travels in a first direction around a perimeter of the housing and a second discharge stream that travels in a second direction around the perimeter of the housing substantially opposite the first direction.

8. The fluorescence analysis system of claim 1, further comprising a locking ring that is configured to mechanically attach the sensor head to the housing so as to fluidly seal the cavity except for fluid communication through the inlet port and the outlet port.

9. The fluorescence analysis system of claim 1, wherein the sensor head includes an elongated sensor housing extending from a proximal end to a distal end, the elongated sensor housing defines a planar bottom surface at the distal end and includes an angular cutout defined by a first planar surface extending radially toward a center of the elongated sensor housing and a second planar surface extending radially toward the center of the elongated sensor housing, wherein the first planar surface intersects the second planar surface, the light source is positioned in the first planar surface, and the detector is positioned in the second planar surface.

10. A flow chamber comprising:
a housing that defines a cavity configured to receive a sensor head and to position the sensor head in a flow of fluid for analysis, the sensor head including at least one light source configured to emit light into the flow of fluid, at least one detector configured to detect fluorescence emissions from the flow of fluid, and a temperature sensor configured to sense a temperature of the flow of fluid;
an inlet port extending through the housing and configured to communicate the flow of fluid from outside of the cavity to an interior of the cavity; and
an outlet port extending through the housing and configured to communicate the flow of fluid from the interior of the cavity to back outside of the cavity,
wherein the housing is configured such that, when the sensor head is inserted into the housing and the flow of fluid enters the housing via the inlet port, the flow of fluid divides into at least a major stream passing through a first physical channel adjacent the light source and the detector and a minor stream passing through a second physical channel adjacent the temperature sensor, the first physical channel being different than the second physical channel.

11. The flow chamber of claim 10, wherein the cavity is configured to receive a sensor head that includes an elongated sensor housing extending from a proximal end to a distal end, the temperature sensor is positioned at the distal end of the elongated sensor housing, and the light source and the detector are positioned between the proximal end and the distal end of the elongated sensor housing, and
wherein the housing is configured such that, when the sensor head is inserted into the housing and the flow of fluid enters the housing via the inlet port, the major stream passes substantially parallel to the elongated sensor housing and the minor stream passes substantially orthogonally to a major axis of the elongated sensor housing.

12. The flow chamber of claim 10, wherein the housing is configured such that, when the sensor head is inserted into the housing and the flow of fluid enters the housing via the inlet port, less than 15 volume percent of the flow of fluid entering the cavity divides toward the minor stream.

13. The flow chamber of claim 10, wherein the housing defines a major axis and the housing is configured such that, when the sensor head is inserted into the housing and the flow of fluid enters the housing via the inlet port, the flow of fluid travels parallel to the major axis, the minor stream divides from the flow of fluid in a direction substantially orthogonal to the major axis, and the major stream is defined as a portion of the flow of fluid that continues past where the minor stream divides from the flow of fluid.

14. The flow chamber of claim 13, wherein the outlet port is positioned approximately opposite the inlet port, and the housing is configured such that, when the sensor head is inserted into the housing and the flow of fluid enters the housing via the inlet port, the major stream and the minor stream recombine within the cavity and discharge through the outlet port.

15. The flow chamber of claim 13, wherein the housing is configured such that, when the sensor head is inserted into the housing and the flow of fluid enters the housing via the inlet port, the major stream divides after passing the light source and detector into a first discharge stream that travels in a first direction around a perimeter of the housing and a second discharge stream that travels in a second direction around the perimeter of the housing substantially opposite the first direction.

16. The flow chamber of claim 10, wherein the housing is configured to receive a locking ring so as to mechanically attach the sensor head to the housing, thereby fluidly sealing the cavity except for fluid communication through the inlet port and the outlet port.

17. The flow chamber of claim 10, wherein the housing is configured to receive a sensor head that includes an elongated sensor housing extending from a proximal end to a distal end, the elongated sensor housing defining a planar bottom surface at the distal end and including an angular cutout defined by a first planar surface extending radially toward a center of the elongated sensor housing and a second planar surface extending radially toward the center of the elongated sensor housing, wherein the first planar surface intersects the second planar surface, the light source is positioned in the first planar surface, and the detector is positioned in the second planar surface.

18. A fluorescence analysis system comprising:
means for detecting fluorescent emissions from a flow of fluid;
means for sensing a temperature of the flow of fluid; and
means for receiving and housing the means for detecting fluorescent emissions and the means for sensing the temperature,
wherein the means for receiving and housing defines a plurality of fluid channels that include at least a major physical fluid channel configured to direct fluid adjacent the means for detecting fluorescent emissions and a minor physical fluid channel configured to direct fluid adjacent the means for sensing the temperature, the major physical fluid channel being different than the minor physical fluid channel.

19. The fluorescence analysis system of claim 18, wherein the minor fluid channel is sized to convey less than 15 volume percent of the flow of fluid entering the means for receiving and housing.

20. The fluorescence analysis system of claim 18, wherein the means for detecting fluorescent emissions and the means for sensing the temperature are positioned within a common housing that is insertable into the means for receiving and the means for housing.

* * * * *